(12) United States Patent
Saruwatari

(10) Patent No.: US 6,727,394 B2
(45) Date of Patent: Apr. 27, 2004

(54) METHOD FOR PRODUCING BISPHENOL A

(75) Inventor: Tetsuya Saruwatari, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 19 days.

(21) Appl. No.: 10/258,571

(22) PCT Filed: Mar. 1, 2002

(86) PCT No.: PCT/JP02/01923

§ 371 (c)(1),
(2), (4) Date: Oct. 30, 2002

(87) PCT Pub. No.: WO02/072515

PCT Pub. Date: Sep. 19, 2002

(65) Prior Publication Data

US 2003/0125587 A1 Jul. 3, 2003

(30) Foreign Application Priority Data

Mar. 8, 2001 (JP) ......................................... 2001-64669

(51) Int. Cl.[7] .............................................. C07C 39/16
(52) U.S. Cl. ...................................................... 568/728
(58) Field of Search ........................................... 568/728

(56) References Cited

U.S. PATENT DOCUMENTS

| 4,391,997 A | 7/1983 | Mendiratta |
| 4,400,555 A | 8/1983 | Mendiratta |
| 6,414,199 B1 | 7/2002 | Saruwatari, et al. |

FOREIGN PATENT DOCUMENTS

| EP | 0 342 758 | 11/1989 |
| JP | 6-25042 | 2/1994 |
| JP | 9-31002 | 2/1997 |

OTHER PUBLICATIONS

Patent Abstracts of Japan, JP 06–025042, Feb. 1, 1994.
Patent Abstracts of Japan, JP 09–031002, Feb. 4, 1997.

*Primary Examiner*—Michael L. Shippen

(57) ABSTRACT

There is disclosed a process for producing bisphenol A by continuously supplying phenol to a first-stage reactor in a continuous multi-stage fixed-bed reaction system composed of at least two reactors each filled in with a cation exchange resin as a catalyst, and continuously supplying acetone separately to each of the reactors, characterized by arranging a reactor which is filled in with a fresh or regenerated cation exchange resin on the final stage in the case of replacing the most seriously deteriorated cation exchange resin in catalytic activity with the fresh or regenerated cation exchange resin, and operating the final stage reactor so that the ratio R of the feed rate of acetone to the consumption rate thereof falls within more than one to less than 3. The above process makes it possible to efficiently produce bisphenol A having favorable hue, while maintaining the acetone feed rate at a relatively low level.

5 Claims, No Drawings

METHOD FOR PRODUCING BISPHENOL A

TECHNICAL FIELD

The present invention relates to an improved process for producing bisphenol A {2, 2-bis(4-hydroxyphenyl) propane}. More particularly, it pertains to a process for efficiently producing bisphenol A having favorable hue as the objective product from phenol and acetone through a continuous multi-stage fixed-bed reaction system in the presence of a cation exchange resin as a catalyst, while maintaining the feed rate of acetone at a relatively low level.

BACKGROUND ART

It is well-known that bisphenol A is an important compound as a starting raw material for epoxy resin or an engineering plastic such as polycarbonate resin and polyarylene resin, and accordingly it tends to increasingly expand its demand year by year.

Bisphenol A is produced by the condensation reaction of excess phenol with acetone in the presence of an acidic catalyst and as the case may be, a sulfur compound as a cocatalyst.

There has heretofore been employed an inorganic mineral acid such as sulfuric acid and hydrogen chloride as an acid catalyst to be used in the reaction. In recent years, however, attention has been paid to cationic exchange resins, which have been brought into industrial applications (refer to UK Patent GB 842209, 849565 and 883391).

On the other hand, it is known that useful sulfur compounds to be used as a cocatalyst include alkyl mercaptans with or without a substituent group such as methyl mercaptan, ethyl mercaptan and thioglycol acid (refer to U.S. Pat. Nos. 2,359,242 and 2,775,620). The mercaptans have a function of increasing the rate of reaction and at the same time, enhancing the selectivity. For instance, in the production of bisphenol A, there are formed as a reaction by-product, 2-(2-hydroxyphenyl)-2-(4-hydroxyphenyl)-propane (o, p'-isomers) as a principal component and in addition thereto, trisphenol and polyphenol. In particular, bisphenol A, when being employed as a starting raw material for polycarbonate resin or polyarylene, is required to be minimized in contents of the above-mentioned by-products, highly pure and free from coloration. As such, the mercaptans are employed to increase the rate of reaction, suppress the formation of the by-products, and enhance the selectivity.

In the case of industrially producing bisphenol A by subjecting phenol and acetone to condensation reaction, there is generally adopted a continuous multi-stage fixed-bed reaction system composed of at least two reactors that are connected in series and each filled in with the aforesaid cation exchange resin as a catalyst.

In such a reaction system, the deterioration of catalyst becomes more serious towards a precedent stage reactor from a succedent stage reactor. As such in the case of replacing the most seriously deteriorated catalyst with a fresh catalyst, when the fresh catalyst is brought in the place of catalyst to be replaced therewith, namely the most precedent stage reactor in the reaction system, there is brought about unfavorable circumstances in that the catalyst as a whole is not effectively utilized, thus lowering the yield of bisphenol A throughout the reactors, whereby deterioration of the catalyst is unfavorably accelerated thereby. In such circumstances, an attempt is made to locate a reactor which is filled inside with a fresh or regenerated cation exchange resin on the most downstream side in the reaction system in replacing the most seriously deteriorated catalyst with the fresh or regenerated catalyst {(refer to Japanese Patent Application Laid-Open No.25042/1994 (Heisei 6)).

Nevertheless, the above-mentioned technique is intended to effectively exhaust the catalyst and thus, further contrivance is necessary in order to maintain the quality of bisphenol A as the objective product. That is to say, when the catalyst becomes deteriorated, the feed rate of acetone is increased to maintain the production (to maintain the conversion of phenol), but in this case there is caused such a problem as an increase in the formation of impurities that are unfavorable for the hue of bisphenol A as the objective product.

On the other hand, there is known a method in which acetone is separately supplied to each of the reactors located in series {(refer to Japanese Patent Application Laid-Open No.19952/1979 (Showa 54)).

DISCLOSURE OF THE INVENTION

Under such circumstances, it is a general object of the present invention to provide a process for efficiently producing bisphenol A having favorable hue as the product from phenol and acetone through a continuous multi-stage fixed-bed reaction system in the presence of a cation exchange resin as a catalyst, while maintaining the feed rate of acetone at a relatively low level.

Other objects of the present invention will become obvious from the text of the specification hereinafter disclosed.

In such circumstances, intensive extensive research and investigation were accumulated by the present inventors in order to achieve the above-mentioned objects. As a result, it has been found that the objects of the present invention can be achieved by separately supplying acetone to each of the reactors in a continuous multi-stage fixed-bed reaction system, arranging a reactor which is filled inside with a fresh or regenerated cation exchange resin on the final stage in the reaction system in replacing the most seriously deteriorated cation exchange resin in catalytic activity with the fresh or regenerated cation exchange resin, and operating the reactor on the final stage so that the ratio of feed rate to the consumption rate for acetone falls within a prescribed range. The present invention has been accomplished on the basis of the foregoing findings and information.

Specifically, the present invention provides a process for producing bisphenol A by continuously supplying phenol to a first-stage reactor in a continuous multi-stage fixed-bed reaction system composed of at least two reactors that are connected in series and each filled in with a cation exchange resin as a catalyst and at the same time, continuously supplying acetone separately to each of the reactors, characterized by arranging a reactor which is filled inside with a fresh or regenerated cation exchange resin on the final stage of the reaction system in replacing the most seriously deteriorated cation exchange resin in catalytic activity with the fresh or regenerated cation exchange resin, and operating the final stage reactor so that the ratio R of the feed rate of acetone to the consumption rate thereof falls within the range of more than one to less than 3.

BEST MODE FOR PRACTICING THE INVENTION

The process according to the present invention is that for producing bisphenol A by subjecting phenol and acetone to condensation reaction through a continuous multi-stage fixed-bed reaction system using a cation exchange resin as a catalyst. The aforesaid cation exchange resin is not specifically limited, but can be selected for use from the cation exchange resins that have hitherto been customarily used as a catalyst for producing bisphenol A. Thus from the viewpoint of catalytic activity and the like, sulfonic acid type cation exchange resin is suitable in particular.

The foregoing sulfonic acid type cation exchange resin is not specifically limited provided that it is a strongly acidic cation exchange resin bearing a sulfonic acid group, but is exemplified by sulfonated styrene/divinyl benzene copolymer, sulfonated and crosslinked styrene polymer, phenol formaldehyde/sulfonic acid resin and benzene formaldehyde/sulfonic acid resin and the like. Any of the exchange resins may be used alone or in combination with at least one other.

In the condensation reaction, mercaptans are usable as a cocatalyst as necessary. The mercaptans, which are the compounds bearing at least one SH group in a free form in a molecule, can be selected for use from alkyl mercaptans and alkyl mercaptans which have at least one substituent such as carboxyl group, amino group and hydroxyl group and which are exemplified by mercaptocarboxylic acid, aminoalkanethiol and mercaptoalcohol. Specific examples of the aforesaid mercaptans include alkyl mercaptans such as ethyl mercaptan, methyl mercaptan, n-butyl mercaptan and n-octyl mercaptan; thiocarboxylic acids such as thioglycol acid and β-mercaptopropionic acid; aminoalkanethiols such as 2-aminoethanethiol and 2, 2-dimethylthiazolidine; and mercaptoalcohols such as mercaptoethanol. Of these compounds, alkyl mercaptans are particularly preferable from the aspect of working effect as a cocatalyst. Any of the mercaptans may be used alone or in combination with at least one other.

Further it is possible to immobilize any of the mercaptans onto the above-mentioned cation exchange resin, and cause the same to function as a cocatalyst.

The amount of the mercaptan to be used is selected in the range of usually 0.1 to 20 mol, preferably 1 to 10 mol based on acetone as a starting raw material.

The ratio of phenol to acetone that are to be used in the process for producing bisphenol A according to the present invention is not specifically limited, but the amount of the unreacted acetone is preferably as small as possible in view of the easiness of refining the resultant bisphenol A, economical efficiency and the like factors. Accordingly, it is advantageous to use excess phenol over a stoichiometric amount thereof. Thus, phenol is used usually in an amount of 3 to 30 mol, preferably 5 to 15 mol per one mol of acetone. In the production of bisphenol A, a reaction solvent is unnecessary in general except for the case where the reaction liquid has unreasonably high viscosity or the reaction is conducted at such a low temperature that the operation is made difficult by solidification.

The condensation reaction between phenol and acetone in the present invention is conducted by continuously supplying phenol and mercaptan to be used at need to a first-stage reactor in a continuous multi-stage fixed-bed reaction system composed of at least two reactors that are connected in series and each filled in with a cation exchange resin as an acid catalyst and at the same time, continuously supplying acetone separately to each of the reactors.

The proportion of acetone to be supplied to each stage of reactors is dependent upon the catalytic activity. For instance, in the case of connecting in series, 3 sets of tower type reactors, that is 3 sets of reaction towers, bisphenol A having stabilized quality is obtainable by setting the load on 10:7:4, approximately from the upstream to downstream sides in the production of bisphenol A.

In the process according to the present invention, in the case of replacing the most seriously deteriorated catalyst with a fresh or regenerated catalyst, which is of service to reaction, there is installed the reactor filled in with the aforesaid fresh or regenerated catalyst on the final stage of the reaction system. The reason is that when the reactor just mentioned is installed precedently to the final stage, there is brought about unfavorable circumstances in that the catalyst as a whole is not effectively utilized, thus lowering the yield of bisphenol A throughout the reactors, whereby deterioration of the catalyst is unfavorably accelerated thereby. In multi-stage reactors, since the deterioration of the catalyst becomes more serious towards a precedent stage reactor from a succedent stage reactor, it is customary to remove the first stage reactor, and install the reactor filled in with the aforesaid fresh or regenerated catalyst on the final stage of the reaction system.

Moreover, in the process according to the present invention the final stage reactor should be operated so that the ratio R of the feed rate of acetone to the consumption rate thereof falls within the range of more than one and less than 3. When the value R is more than 3, bisphenol A as the objective product is deteriorated in hue.

In the following, some description will be given of the reaction conditions of the continuous multi-stage fixed-bed reaction system.

Firstly, the acetone/phenol molar ratio is selected in the range of usually 1/30 to 1/3, preferably 1/15 to 1/5. The molar ratio, when being less than 1/30, brings about a fear of an unreasonably low rate of reaction, whereas the molar ratio, when being more than 1/3, results in a tendency to form an excessive amount of impurities, and lower the selectivity to bisphenol A. On the other hand, when the mercaptan is not immobilized on the cation exchange resin, the mercaptan/acetone molar ratio is selected in the range of usually 0.1/100 to 20/100, preferably 1/100 to 10/100. The molar ratio, when being less than 0.1/100, causes a fear of incapability of sufficiently exhibiting the working effect on enhancing the rate of reaction or the selectivity to bisphenol A, whereas the molar ratio, when being more than 20/100, results in that the working effect on enhancing the same is not so recognized considering such a large amount.

Further the reaction temperature is selected in the range of usually 40 to 150° C., preferably 60 to 110° C. The reaction temperature, when being lower than 40° C., gives rise to an unreasonably low rate of reaction and besides, extremely high viscosity of the reaction liquid, thereby causing a fear of solidification as the case may be. On the contrary, the reaction temperature, when being higher than 150° C., leads to difficulty in reaction control, deterioration of selectivity to bisphenol A(p, p'-isomer) and further decomposition or deterioration of the cation exchange resin as the catalyst. The LHSV (liquid hourly space velocity) is selected in the range of usually 0.2 to 30 $hr^{-1}$, preferably 0.5 to 10 $hr^{-1}$.

In the process according to the present invention, the reaction mixture coming out from the reaction tower is post-treated by a well known method so that the objective bisphenol A is collected. In the following some description will be given of one example of the post-treatment. Firstly, concentration of the reaction mixture is carried out prior to crystallization. The conditions of the concentration are not specifically limited, but usually include a temperature in the range of 130 to 170° C. and a pressure in the range of 13 to 53 kPa. The temperature, when being lower than 130° C., necessitates a high degree of vacuum, whereas the temperature, when being higher than 170° C., brings about an increase in amounts of impurities or the cause for coloration of the reaction product. It is advantageous that the concentration of bisphenol A in the concentrated residual liquid ranges from 25 to 40% by weight. The concentration thereof, when being lower than 25% by weight, results in a low recovery rate of bisphenol A, whereas the concentration thereof, when being higher than 40% by weight, causes difficulty in slurry transport after crystallization.

The crystallization of bisphenol A and phenol adducts from the concentrated residual liquid is usually conducted by a vacuum cooling crystallization method which comprises cooling under reduced pressure taking advantage of the latent heat of water vaporization. In the aforesaid method, crystallization treatment is performed usually under the conditions including a temperature in the range of 40 to 70° C. and a pressure in the range of 3 to 13 kPa by adding water in an amount of 3 to 20% by weight approximately to the concentrated residual liquid. The water to be added, when being less than 3% by weight, causes insufficient heat-removal capacity, whereas the water, when being more than 20% by weight, unfavorably leads to an increase in dissolution loss of bisphenol A. Moreover, A crystallization temperature, when being lower than 40° C., gives rise to a fear of an increase in the viscosity of crystallization liquid or solidification of the same, whereas the temperature, when being higher than 70° C., unfavorably brings about an increase in dissolution loss of bisphenol A.

Subsequently, the bisphenol A and phenol adducts that have been crystallized in such a manner are separated by a well known method and thereafter are subjected to a cleaning treatment with phenol. Then the adducts that have been subjected to a cleaning treatment are separated into bisphenol A and phenol under the conditions including a temperature selected in the range of usually 130 to 200° C., preferably 150 to 180° C. and a pressure selected in the range of 3 to 20 kPa.

The residual phenol in the bisphenol A obtained by the separation treatment is removed to a substantially complete extent by steam stripping method or the like method, whereby bisphenol A with high quality is obtained.

In what follows, the present invention will be described in more detail with reference to comparative examples and working examples, which however shall never limit the present invention thereto.

EXAMPLE 1

Three sets of reaction towers were connected in series which were each filled in with a cation exchange resin composed of sulfonated styrene/divinylbenzene copolymer (manufactured by Mitsubishi Chemical Industries Ltd. under the trade name "Diaion SK-104H"). Subsequently, the first stage reaction tower was charged with a mixture of phenol and ethyl mercaptan at an LHSV of 1 hr¹, while supplying acetone separately to each of the reaction towers, wherein the molar ratio of phenol/total acetone was 1/10, the molar ratio of ethyl mercaptan/total acetone was 1/20, and the inlet temperature in each of the reaction towers was set on 75° C.

The catalyst in the first stage reaction tower, which was deteriorated in its catalytic activity with the proceeding of the reaction, was replaced with a fresh catalyst. Thus the reaction tower was placed in the final stage, the previously second stage reaction tower was placed in the first stage, and the previously third stage reaction tower was placed in the second stage. Even after the reshuffle of the reaction towers, it was possible to maintain the running without reducing the production rate, while suppressing the value R to less than 3. The value R before and after the reshuffle of the reaction towers and the hue of the bisphenol A as the objective product are given in Table 1.

Therein the hue of the bisphenol A was visually evaluated by heating the same in an atmosphere of air at 220° C. for 40 minutes by the use of APHA standard color.

Comparative Example 1

In the same manner as in Example 1, three sets of reaction towers were connected in series which were each filled in with the cation exchange resin same as in Example 1. Subsequently, the first stage reaction tower was charged with a mixture of phenol and ethyl mercaptan at an LHSV of 1 hr⁻¹, while supplying acetone separately to each of the reaction towers, wherein the molar ratio of phenol/total acetone was 1/10, the molar ratio of ethyl mercaptan/total acetone was 1/20, and the inlet temperature in each of the reaction towers was set on 75° C.

The catalyst in the first stage reaction tower, which was deteriorated in its catalytic activity with the proceeding of the reaction, was replaced with a fresh catalyst, but the reshuffle of the reaction towers was not conducted differently from Example 1.

The value R before and after the reshuffle of the catalyst and the hue of the bisphenol A as the objective product are given in Table 1.

TABLE 1

| | | R | | | Hue of |
| | | First Stage | Second Stage | Third Stage | product {APHA} |
|---|---|---|---|---|---|
| Example 1 | before reshuffle of reaction towers | 2.0 | 2.0 | 2.5 | 10 |
| | after reshuffle of reaction towers | 2.0 | 2.0 | 2.0 | 10 |
| Comp'tive Example 1 | before reshuffle of catalyst | 2.2 | 1.9 | 2.9 | 10 |
| | after reshuffle of catalyst | 1.1 | 2.1 | 3.4 | 15 |

Industrial Application

According to the present invention, it is made possible to efficiently produce bisphenol A having favorable hue, while maintaining the feed rate of acetone at a relatively low level by virtue of the process for producing the bisphenol A from phenol and acetone using a a continuous multi-stage fixed-bed reactors filled in with cation exchange resin, wherein the ratio R of the feed rate of acetone to the consumption rate thereof in the final stage reactor falls within the range of more than one and less than 3.

What is claimed is:

1. A process for producing bisphenol A by continuously supplying phenol to a first-stage reactor in a continuous multi-stage fixed-bed reaction system composed of at least two reactors that are connected in series and are each filled in with a cation exchange resin as a catalyst and at the same time, continuously supplying acetone separately to each of the reactors, characterized by arranging a reactor which is filled in with a fresh or regenerated cation exchange resin on the final stage of the reaction system in replacing the most seriously deteriorated cation exchange resin in catalytic activity with the fresh or regenerated cation exchange resin, and operating the final stage reactor so that the ratio R of the feed rate of acetone to the consumption rate thereof falls within the range of more than one to less than 3.

2. The process for producing bisphenol A according to claim 1, wherein the cation exchange resin is a strongly acidic sulfonic acid type ion exchange resin.

3. The process for producing bisphenol A according to claim 1, wherein mercaptan is used as a cocatalyst in the reaction system along with the cation exchange resin.

4. The process for producing bisphenol A according to claim 3, wherein the mercaptan is an alkyl mercaptan.

5. The process for producing bisphenol A according to claim 1, wherein the phenol and acetone are subjected to reaction under the conditions including an acetone/phenol molar ratio in the range of 1/30 to 1/3 and a reaction temperature in the range of 40 to 150° C.

* * * * *